US006083170A

United States Patent [19]
Ben-Haim

[11] Patent Number: 6,083,170
[45] Date of Patent: *Jul. 4, 2000

[54] SELF-ALIGNING CATHETER

[75] Inventor: Shlomo Ben-Haim, Haifa, Israel

[73] Assignee: Biosense, Inc., New Brunswick, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/180,740

[22] PCT Filed: May 15, 1997

[86] PCT No.: PCT/IL97/00159

§ 371 Date: Jan. 14, 1999

§ 102(e) Date: Jan. 14, 1999

[87] PCT Pub. No.: WO97/44089

PCT Pub. Date: Nov. 27, 1997

Related U.S. Application Data

[60] Provisional application No. 60/017,634, May 17, 1996, abandoned, and provisional application No. 60/034,703, Jan. 3, 1997, abandoned.

[51] Int. Cl.[7] .................................................. A61B 8/12
[52] U.S. Cl. ...................................... 600/463; 600/462
[58] Field of Search .......................... 604/528; 600/462, 600/463, 471, 439, 117, 118, 467; 606/159

[56] References Cited

U.S. PATENT DOCUMENTS

| Re. 34,502 | 1/1994 | Webster, Jr. | 607/125 |
|---|---|---|---|
| 3,726,269 | 4/1973 | Webster, Jr. | 128/2.05 F |
| 4,535,757 | 8/1985 | Webster, Jr. | 128/1 D |
| 4,554,928 | 11/1985 | Webster, Jr. | 128/709 |
| 4,570,354 | 2/1986 | Hindes | 33/534 |
| 4,576,177 | 3/1986 | Webster, Jr. | 128/660 |
| 4,921,482 | 5/1990 | Hammerslag et al. | 604/95 |
| 4,960,134 | 10/1990 | Webster, Jr. | 128/786 |
| 5,057,092 | 10/1991 | Webster, Jr. | 604/282 |
| 5,078,714 | 1/1992 | Katims | 606/38 |
| 5,195,968 | 3/1993 | Lundquist et al. | 604/95 |
| 5,217,484 | 6/1993 | Marks | 606/200 |
| 5,267,960 | 12/1993 | Hayman et al. | 604/106 |
| 5,295,484 | 3/1994 | Marcus et al. | 128/660.03 |
| 5,295,486 | 3/1994 | Wollschläger et al. | 128/661.01 |
| 5,368,564 | 11/1994 | Savage | 604/95 |
| 5,368,592 | 11/1994 | Stern et al. | 606/33 |
| 5,373,849 | 12/1994 | Maroney et al. | 128/662.06 |
| 5,383,923 | 1/1995 | Webster, Jr. | 607/125 |
| 5,385,148 | 1/1995 | Lesh et al. | 128/662.06 |
| 5,386,741 | 2/1995 | Rennex | 74/490 |
| 5,391,199 | 2/1995 | Ben-Haim | 607/122 |
| 5,411,025 | 5/1995 | Webster, Jr. | 128/642 |
| 5,423,321 | 6/1995 | Fontenot | 128/664 |
| 5,423,882 | 6/1995 | Jackman et al. | 607/122 |
| 5,431,168 | 7/1995 | Webster, Jr. | 128/658 |
| 5,450,846 | 9/1995 | Goldreyer | 128/642 |
| 5,522,873 | 6/1996 | Jackman et al. | 607/122 |

(List continued on next page.)

FOREIGN PATENT DOCUMENTS

| WO 94/00050 | 1/1994 | WIPO | A61B 5/02 |
|---|---|---|---|
| WO 95/05773 | 3/1995 | WIPO | A61B 5/042 |
| WO 95/10226 | 4/1995 | WIPO | A61B 5/04 |
| WO 95/19738 | 7/1995 | WIPO | A61B 17/36 |
| WO 96/05768 | 2/1996 | WIPO | |
| WO 97/24983 | 7/1997 | WIPO | A61B 5/042 |
| WO 97/29684 | 8/1997 | WIPO | A61B 5/05 |
| WO 97/29701 | 8/1997 | WIPO | A61B 17/22 |

Primary Examiner—Michael Buiz
Assistant Examiner—Kevin Truong
Attorney, Agent, or Firm—Louis J. Capezzuto

[57] ABSTRACT

A flexible, elongate probe having a distal end for insertion through physiological tissue, preferably through a lumen in the tissue. The probe includes a sensor, which generates signals indicative of a characteristic of the tissue in a vicinity of the probe, and an alignment mechanism, which deflects the distal end of the probe in response to the signals. The signals may be indicative of obstructions or of the direction of a clear channel in the lumen. The sensor preferably comprises one or more ultrasound transducers.

31 Claims, 8 Drawing Sheets

U.S. PATENT DOCUMENTS

| | | | |
|---|---|---|---|
| 5,555,883 | 9/1996 | Avitall | 128/642 |
| 5,558,093 | 9/1996 | Pomeranz | 600/463 |
| 5,569,220 | 10/1996 | Webster, Jr. | 604/282 |
| 5,588,432 | 12/1996 | Crowley | 128/660.03 |
| 5,596,989 | 1/1997 | Morita | 600/463 |
| 5,626,136 | 5/1997 | Webster, Jr. | 128/642 |
| 5,628,313 | 5/1997 | Webster, Jr. | 128/642 |
| 5,662,116 | 9/1997 | Kondo et al. | 600/462 |
| 5,772,590 | 6/1998 | Webster, Jr. | 600/374 |
| 5,782,239 | 7/1998 | Webster, Jr. | 128/642 |
| 5,797,870 | 8/1998 | March et al. | 604/49 |

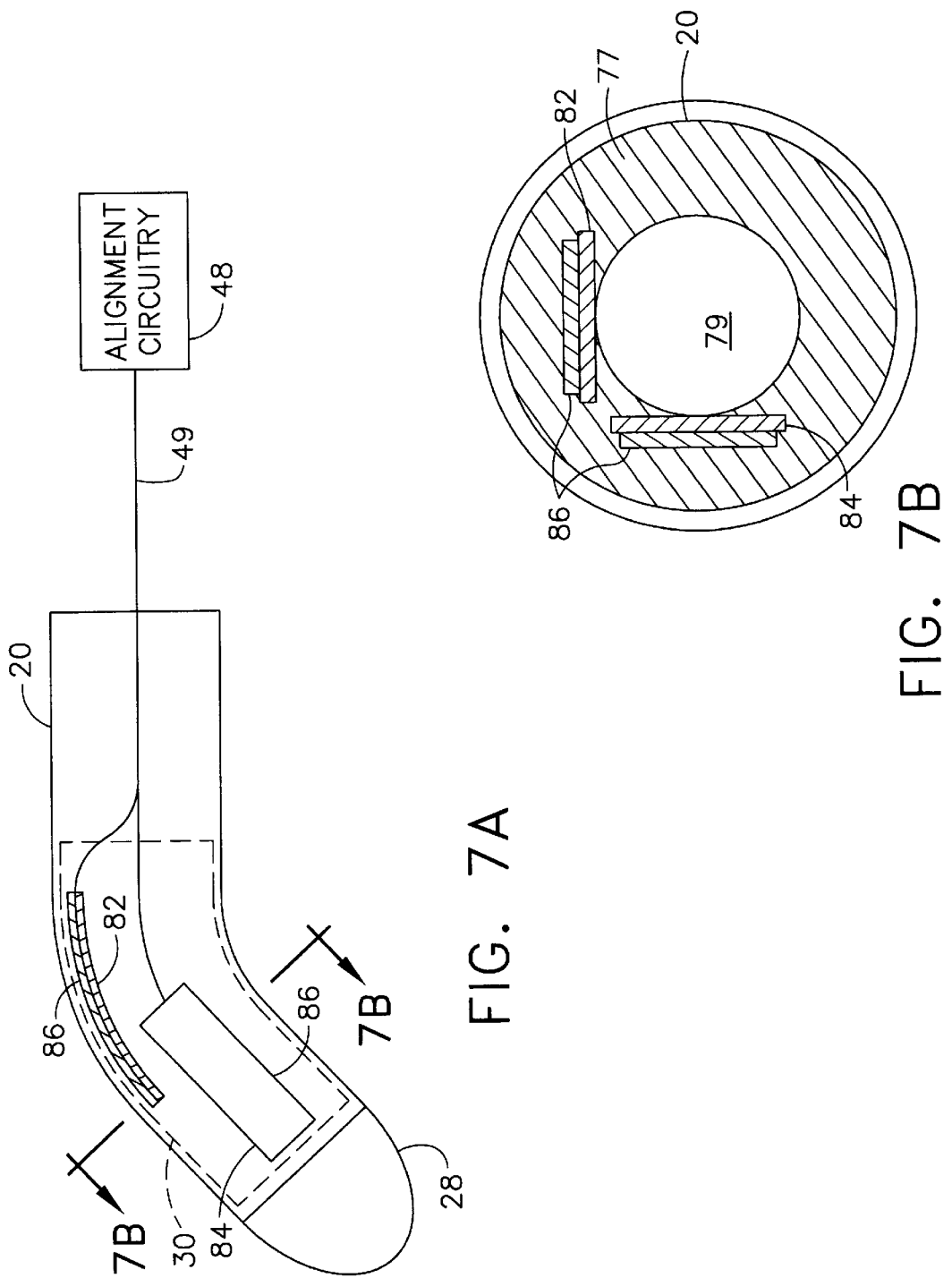

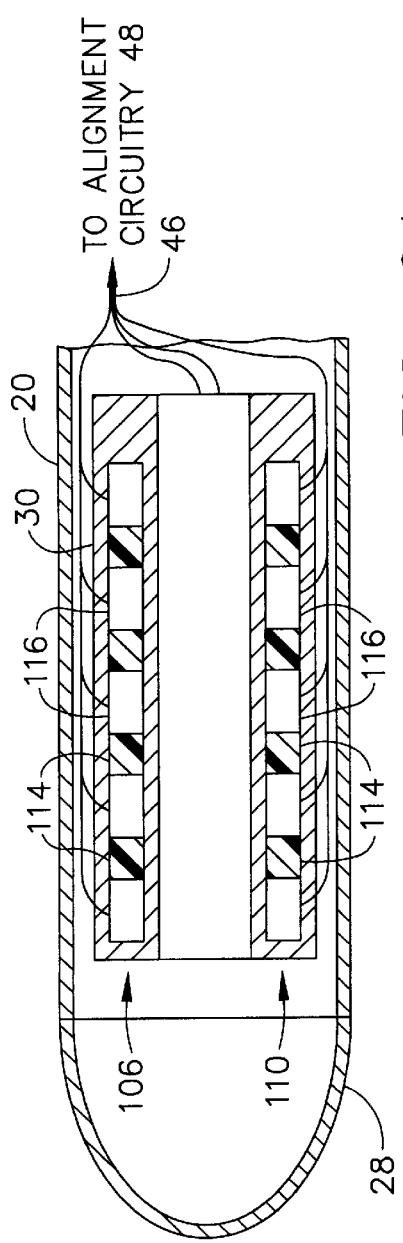
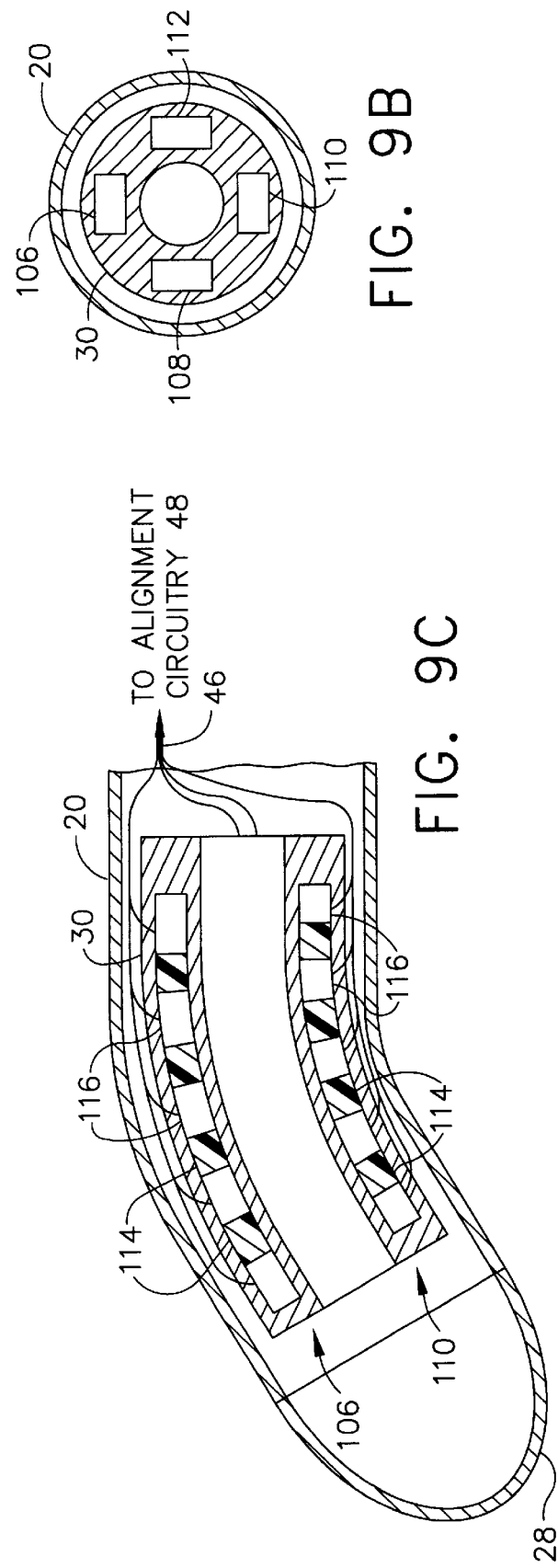

SELF-ALIGNING CATHETER

RELATED APPLICATIONS

This patent application claims the benefit of U.S. Provisional Patent Application Ser. No. 60/017,634, filed May 17, 1996 now abandoned, and of U.S. Provisional Patent Application Ser. No. 60/034,703, filed Jan. 3, 1997 now abandoned.

FIELD OF THE INVENTION

The present invention relates generally to systems for medical diagnosis and treatment, and specifically to intravascular medical catheters.

BACKGROUND OF THE INVENTION

Flexible catheters are commonly used for invasive diagnostic and therapeutic procedures in the cardiovascular system. Such catheters are inserted percutaneously into a vein or artery, and then guided by the physician to the desired location in the blood vessels or heart. Generally, curves present in the blood vessels result in the catheter being urged against the blood vessel wall as the catheter progresses.

Pathological conditions, for example local stenoses, may cause blood vessels to narrow and impede the movement of the catheter. If the physician attempts to push the catheter past such a stenosis, the force may cause a dissection of the wall of the blood vessel or break loose a large piece of plaque, which can then lodge in a downstream vessel and impede blood flow there. For this reason, cardiovascular catheterization of atherosclerotic patients and others having pathologies of the vascular system is frequently a painful and difficult procedure.

Physicians commonly use fluoroscopy or other imaging techniques to assist them in visualizing the location of the catheter inside the body and guiding the catheter to the desired location. Fluoroscopy, however, exposes the patient to undesirable radiation. Furthermore its ability to detect narrowings of the blood vessels is limited, requiring the injection of a radio-opaque contrast medium or radioactive marker substance into the bloodstream, and its usefulness is generally limited to gross navigation of the catheter.

Some catheters include means for steering their distal tips, which the physician can use to guide the catheter around curves and past obstructions such as narrowed blood vessels. However, they give the physician no advance warning to prevent the catheter from striking obstructions, such as local stenoses, in the blood vessels or to assist in maneuvering the catheter around such obstructions.

U.S. Pat. No. 5,492,131, to Galel, which is incorporated herein by reference, describes a catheter system in which a catheter is advanced through a physiological lumen in a fully automatic manner, navigating according to a pre-determined "road map" of the lumen. A position sensor adjacent to the distal end of the catheter is used to provide feedback for catheter navigation.

SUMMARY OF THE INVENTION

It is, therefore, an object of some aspects of the present invention to provide a catheter having a sensor, which detects obstructions in the catheter's path as it advances through a blood vessel or other physiological lumen or channel, and aids in preventing collision of the catheter with such obstructions.

It is a further object of some aspects of the present invention to provide a catheter having a self-alignment mechanism, which deflects the distal end of the catheter, automatically or under operator control, so as to navigate along a desired path through physiological tissue and, preferably, to avoid collisions with obstructions in the catheter's path.

In preferred embodiments of the present invention, an intravascular catheter includes a sensor, adjacent to the catheter's distal tip, for detecting obstructions in the blood vessel ahead of the catheter and a mechanism preferably an automatic mechanism, for deflecting the catheter's distal tip so as to prevent frontal contact of the catheter with such obstructions.

Preferably, the sensor and the deflection mechanism constitute a closed-loop servo system, which maintains the distal end of the catheter in a desired position, most preferably along or adjacent to a central axis of the blood vessel.

In some preferred embodiments of the present invention, the sensor comprises one or more ultrasound transducers. The sensor emits ultrasound waves into the blood vessel ahead of the catheter and receives ultrasound signals reflected from material in the blood vessel, wherein such material may be solid and/or liquid.

In some preferred embodiments of the present invention, two or more ultrasound transducers are arrayed at the distal end of the catheter, in such manner that each of the transducers receives ultrasound signals in a respective, preferred direction.

In some preferred embodiments of the present invention, the angular orientations of one or more ultrasound transducers at the distal end of the catheter, each of which transducers receives ultrasound signals in a respective, preferred direction, are swept mechanically, so as to scan an area ahead of the catheter.

In other preferred embodiments of the present invention, the sensor comprises a phased array of ultrasound transducers, which emits an ultrasound beam in a preferred direction. The beam is swept electronically by scanning circuitry, as is known in the art, so as to scan an area ahead of the catheter.

In preferred embodiments of the present invention, the transducers are coupled to signal processing circuitry, which analyzes the signals from the transducers so as to determine the likely position of an obstruction ahead of the catheter. Such "obstructions" may be stenoses or curves in the blood vessel.

In some preferred embodiments of the present invention, the signal processing circuitry measures the Doppler shift of the ultrasound signals, so as to track the flow of blood in the blood vessel ahead of the catheter. Variations in blood flow velocity are used to determine the likely position of an obstruction ahead of the catheter.

Preferably the circuitry determines the area having maximal flow velocity in a cross-section of the blood vessel ahead of the catheter. It will be appreciated by those skilled in the art that the area having maximal flow volume is generally unobstructed.

In still other preferred embodiments of the present invention, the sensor comprises a proximity detector, of a type known in the art, which detects the presence of an obstruction ahead of the catheter, when the distal tip of the catheter is oriented so that the proximity detector is pointing toward the obstruction.

In some preferred embodiments of the present invention, alignment circuitry receives information from the signal processing circuitry or from the proximity detector regarding an obstruction or curve ahead of the catheter, and determines a desired deflection of the distal end of the catheter so as to avoid collision with the obstruction or curve. Preferably the alignment circuitry drives the distal tip deflection mechanism, so as to steer the catheter around the obstruction or curve and align the catheter to pass through an unobstructed portion of the blood vessel or other lumen.

In some preferred embodiments of the present invention, the alignment circuitry drives the distal tip deflection mechanism so as to steer the catheter toward the area of maximal flow. It will be appreciated that steering the catheter toward the area of maximal flow will generally cause the catheter to avoid collisions with obstructions and to turn smoothly through curves in the blood vessels.

In other preferred embodiments of the present invention, the catheter includes a position sensor, adjacent to the catheter's distal tip, which allows the coordinates of the tip to be determined relative to an external frame of reference. A map or image of the blood vessels or other physiological lumens through which the catheter is to pass is acquired by angiography, MRI or other methods, known in the art, and is registered with the frame of reference relative to which the coordinates of the tip are to be determined. As the catheter is advanced through the vessels or other lumens, its position is tracked, using the position sensor, relative to the map or image, and the distal tip of the catheter is deflected so as to steer it along a desired path through the vessels or other lumens and to avoid collision with obstructions therein.

The position sensor preferably comprises one or more coils, which generate signals in response to an externally-applied magnetic field, as described, for example in U.S. Pat. No. 5,391,199 and PCT patent application number PCT/US95/01103, filed Jan. 24, 1995, which are assigned to the assignee of the present application and whose disclosures are incorporated herein by reference. Other types of position sensors, known in the art, may similarly be used, however.

Alternatively or additionally, the position sensor may be used in a similar manner in conjunction with other previously-acquired and stored data regarding features of the blood vessels or other lumens through which the catheter is to pass. Such data may include, for example, information regarding the positions of curves, bifurcations and/or obstructions in the blood vessels, measured or otherwise acquired during an earlier catheterization or a surgical procedure.

Furthermore, a plurality of position sensors, or a combination of position sensors and bend sensors, may be used to determine not only the position of the catheter's distal tip, but also the course of an entire distal portion of the catheter within the body, preferably as described in U.S. Provisional Patent Application Ser. No. 60/034,703, filed Jan. 3, 1997, which is assigned to the assignee of the present patent application and whose disclosure is incorporated herein by reference. Knowing the course of the distal portion of the catheter is useful both in registering the catheter position with a map of a physiological lumen, as described above, and in determining the position of the catheter within a larger physiological cavity, for example, a chamber of the heart.

Many types of tip deflection mechanism are known in the art, and the inventive principles of the present invention may be generally applied to any catheters having a suitable tip deflection mechanism. While certain tip deflection mechanisms are included in the preferred embodiments of the present invention described below, these mechanisms are included here by way of example, and should not be construed as limiting the scope of some aspects of the invention.

In preferred embodiments of the present invention, the distal tip deflection mechanism comprises one or more bendable elements, inside the catheter and adjacent to its distal tip. These elements are controlled by alignment circuitry so as to maintain the distal end of the catheter in a substantially straight orientation, so long as no obstruction is detected immediately ahead of the catheter. When an obstruction is detected, however, the alignment circuitry causes at least one of the one or more bendable elements to bend, so as to steer the catheter around the obstruction and align the catheter to pass through an unobstructed portion of the blood vessel or other lumen.

In some preferred embodiments of the present invention, the one or more bendable elements comprise shape memory material, such as NiTi, or other such materials known in the art. The elements are formed so that when they are below a known temperature, they remain substantially flexible and are maintained in a first, known alignment, preferably substantially straight. When one of the elements is heated to above the known temperature, however, it assumes a second, different form, preferably bent and substantially rigid, thereby causing the distal end of the catheter to deflect.

In one such preferred embodiment of the present invention, the tip deflection mechanism includes one or more heating elements of a type known in the art, for example heating coils, respectively associated with the shape memory elements. The alignment circuitry generates electrical currents, which are passed through the heating coils and heat the bendable elements so as to maintain them in their substantially flexible state and straight alignment. When the current to one or more of the heating coils is turned off or reduced, the respective bendable element cools to below its critical temperature, and thereby assumes its substantially rigid, bent form.

In other preferred embodiments of the present invention, the one or more bendable elements comprise one or more bimetal elements, of types known in the art, which bend or straighten in response to changes in temperature. The tip deflection mechanism further preferably includes heating and/or cooling elements, as described above, which control the respective bend angles of the bimetal elements, so as to straighten or deflect the distal end of the catheter.

In still other preferred embodiments of the present invention, one or more mechanical pull-wires are associated with the one or more bendable elements. Each such pull-wire is coupled distally to a bendable element and proximally to an alignment mechanism. This mechanism applies a variable tension to the pull-wire, thereby causing the bendable element to which the pull-wire is coupled to bend or straighten as required.

In further preferred embodiments of the present invention, the distal tip deflection mechanism comprises one or more piezoelectric elements. These elements are controlled by alignment circuitry so as to maintain the distal end of the catheter in a substantially straight orientation, so long as no obstruction is detected immediately ahead of the catheter. When an obstruction is detected, however, the alignment circuitry causes a voltage to be applied to at least one of the one or more piezoelectric elements, so as to alter a dimension of the element and thereby deflect the distal end of the catheter, as described above.

In preferred embodiments of the present invention, the distal tip deflection mechanism comprises two or more elements, which may be bendable elements, piezoelectric elements or elements of other types known in the art, which function to deflect the distal tip in two or more different radial directions, for example, left-right and up-down, relative to the long axis of the catheter. These elements are preferably controlled by alignment circuitry so as to deflect the distal tip of the catheter in any desired direction.

Alternatively, in other preferred embodiments of the present invention, the distal tip deflection mechanism may deflect the distal tip of the catheter in only a single direction relative to the catheter axis. A catheter rotation mechanism, preferably coupled to the proximal end of the catheter, rotates the catheter about its long axis. This rotation mechanism, along with the distal tip deflection mechanism, is preferably controlled by alignment circuitry so that the catheter's distal tip may be automatically deflected in any desired direction, so as to avoid obstructions and navigate through curves in the vasculature.

In some preferred embodiments of the present invention, the alignment circuitry includes an operator interface, which enables the operator to steer the catheter by controlling the distal tip deflection mechanism.

In some preferred embodiments of the present invention, the catheter is further coupled to a catheter advance mechanism, which is controlled by alignment circuitry so as to advance the catheter gradually, manually or automatically, through the blood vessel, while avoiding collision with obstructions, as described above.

Although the above preferred embodiments are described with reference to intravascular catheters, it will be appreciated that the principles of the present invention may be applied to produce self-aligning probes for insertion through physiological tissues and cavities of other types. Such probes may comprise sensors which detect characteristics of fluid flow and/or pressure and/or solid obstructions in the path of the probe, as described above. Alternatively or additionally, the probes may include sensors of other types, for example, chemical sensors or electrical sensors, as are known in the art. Thus, in one exemplary embodiment of the present invention, a probe for insertion into the liver of a subject comprises a chemical sensor adjacent its distal end, which may be used for detecting elevated hormonal activity, for example, and a self-alignment mechanism, as described above, for guiding the probe toward a source of the hormonal activity.

There is therefore provided, in accordance with a preferred embodiment of the present invention, a flexible, elongate probe having a distal end for insertion through physiological tissue, including:

a sensor, which generates signals indicative of a characteristic of the tissue in a vicinity of the probe; and an alignment mechanism, which deflects the distal end of the probe in response to the signals.

Preferably, the probe includes a catheter for insertion through a physiological lumen, and the sensor generates the signals responsive to a characteristic of the lumen ahead of the catheter.

Preferably, the signals are indicative of obstructions in the lumen. Alternatively or additionally, the signals are indicative of the direction of a clear channel in the lumen.

Further preferably, the signals are indicative of a fluid flow in the tissue, most preferably of a gradient of the flow, or alternatively of turbulence of the flow.

Preferably, the alignment mechanism drives the probe toward an area of high flow velocity.

Alternatively or additionally, the signals are indicative of a pressure in the tissue, preferably of a gradient of the pressure, and the alignment mechanism drives the probe toward the leading edge of a pressure wave in the tissue.

In a preferred embodiment of the invention, the signals are indicative of chemical activity in the tissue.

Preferably, the sensor includes at least one ultrasound transducer, which generates and receives ultrasound waves. Further preferably, signal processing circuitry detects a Doppler shift in the ultrasound waves received by the sensor.

Alternatively or additionally, the sensor includes a plurality of ultrasound transducers, preferably a phased array of ultrasound transducers, which detect reflection of ultrasound waves from a plurality of respective preferred directions.

In a preferred embodiment of the invention, the sensor includes a proximity detector.

In other preferred embodiments, the sensor includes an infrared detector and/or an optical detector and/or a pressure sensor and/or a position sensor.

Preferably, the sensor includes a detector array. Additionally or alternatively, a mechanical scanner scans the sensor.

Preferably, the alignment mechanism includes a plurality of deflection elements, each of which deflects the probe in one of a plurality of respective directions.

Alternatively, the alignment mechanism includes one or more deflection elements that deflect the distal end of the probe and a rotation element that rotates the probe about its long axis.

Preferably, at least one of the deflection elements includes a bendable element.

Preferably, the bendable element includes superelastic material or, additionally or alternatively, a bimetal element.

Preferably, the bendable element bends or straightens in response to an electrical drive signal, which preferably causes a change in the temperature of the bendable element. Preferably, a heating element, associated with the bendable element, receives the electrical drive signal. Additionally or alternatively, a cooler, associated with the bendable element, receives the electrical drive signal.

In a preferred embodiment of the invention, at least one mechanical pull-wire is coupled to the bendable element, which bends in response to tension in the pull-wire.

In another preferred embodiment, at least one of the deflection elements includes at least one piezoelectric stack, preferably a plurality of piezoelectric crystals, coupled by a plurality of bendable joints, wherein the stack bends in response to an electrical signal applied thereto.

Preferably, the probe includes a probe advance mechanism, which advances the probe gradually through the tissue.

Preferably, a closed-loop servo system, which maintains the distal end of the probe in a desired position, most preferably substantially aligned with a central axis of a clear channel in the tissue.

There is further provided, in accordance with a preferred embodiment of the present invention, a method for passing a probe, having a sensor at a distal end thereof, through physiological tissue, including:

sensing a characteristic of the tissue, using the sensor;

determining a desired direction of motion of the probe, based on the characteristic; and deflecting the probe in the desired direction.

Preferably, passing the probe through physiological tissue includes passing the probe through a channel in the tissue, and sensing the characteristic of the tissue includes sensing a characteristic of material in or adjacent to the channel, most preferably sensing an obstruction in the channel by receiving ultrasound waves reflected from the obstruction.

Alternatively or additionally, sensing the obstruction includes forming an image of the obstruction and/or determining a distance from the probe to the obstruction.

Further alternatively or additionally, sensing the characteristic of the tissue includes sensing a flow velocity in the tissue, preferably by receiving Doppler-shifted ultrasound waves and/or by identifying an area of turbulence. Preferably, determining the desired direction of motion includes finding an axis of the channel along which flow velocity is generally greatest.

In a preferred embodiment of the invention, sensing the characteristic of the tissue includes sensing a pulsatile pressure, and determining the desired direction of motion includes finding an axis of motion that is generally coincident with the leading edge of a pressure wave in the tissue.

There is also provided, in accordance with a preferred embodiment of the present invention, a method for passing a probe, having a position sensor at a distal end thereof, through a physiological channel, including:

generating a map of the channel by forming an image of physiological structures including the channel;

sensing the position of the distal end of the probe relative to the map, using the position sensor;

determining a desired direction of motion of the probe, based on the map; and deflecting the probe in the desired direction.

Preferably, generating a map of the channel includes probing the channel and recording features thereof Preferably, deflecting the probe includes applying an electrical current to an element therein and/or applying mechanical tension to an element therein. Additionally or alternatively, deflecting the probe includes rotating the probe.

Preferably, deflecting the probe includes steering the probe around a curve in the channel.

Preferably, the method described above further includes mechanically driving the probe to pass it through the channel.

The present invention will be more fully understood from the following detailed description of the preferred embodiments thereof, taken together with the drawings in which:

BRIEF DESCRIPTION OF THE DRAWINGS

FIG. 7A is a schematic representation of a catheter in accordance with another preferred embodiment of the present invention;

FIG. 7B is a cross-sectional view of the preferred embodiment shown in FIG. 7A;

FIG. 9A is a schematic representation of a catheter in accordance with another preferred embodiment of the present invention;

FIG. 9B is a cross-sectional view of the preferred embodiment shown in FIG. 9A;

FIG. 9C is a schematic representation of the preferred embodiment shown in FIGS. 9A and 9B, showing deflection of the distal end of the catheter.

DETAILED DESCRIPTION OF PREFERRED EMBODIMENTS

Figure 1A:
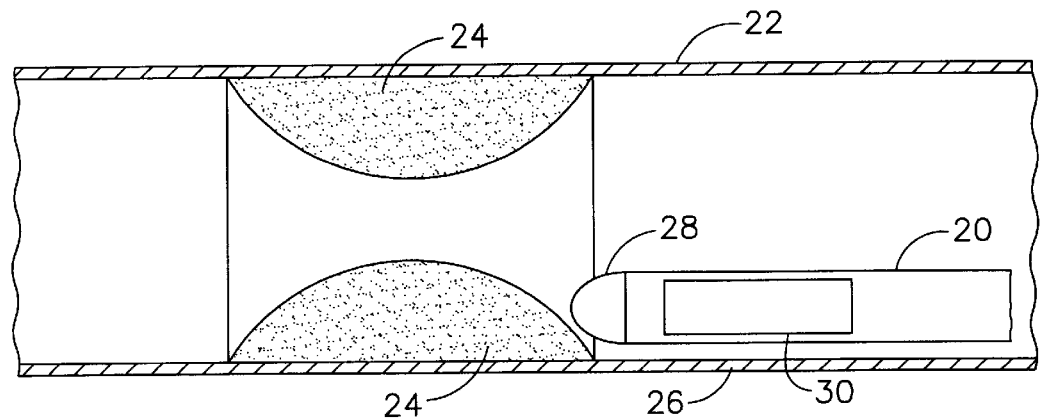
FIGS. 1A and 1B are schematic representations of a catheter encountering an obstruction in a blood vessel (FIG. 1A) and aligned so as to bypass the obstruction (FIG. 1B), in accordance with a preferred embodiment of the present invention.
Figure 1B:
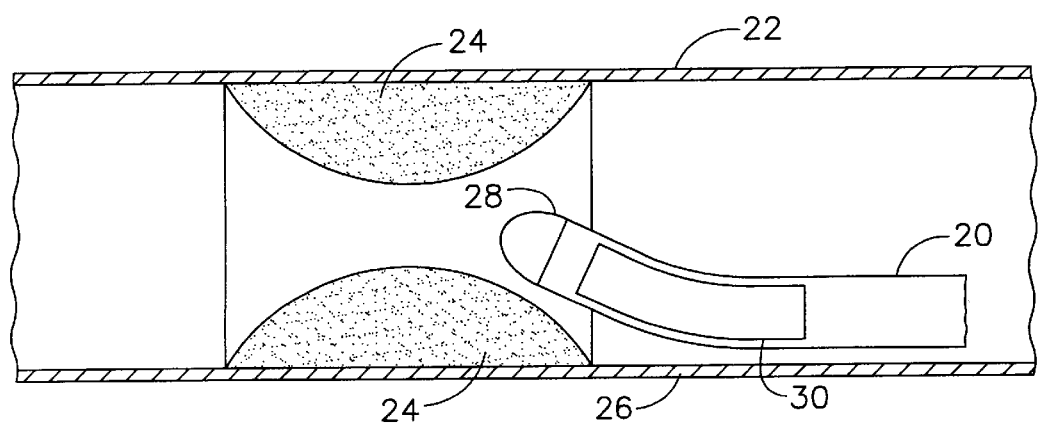

Reference is now made to FIGS. 1A and 1B, which schematically illustrate the functioning of preferred embodiments of the present invention. As shown in FIG. 1A, catheter 20 advances through blood vessel 22, where it encounters a stenosis 24, at which blood vessel 22 narrows. Catheter 20 is generally flexible enough to pass around curves in the blood vessels, but is stiff enough to maintain its forward orientation and prevent buckling under forces encountered during its insertion and travel. This stiffness normally urges the catheter to a position adjacent to a wall 26 of the blood vessel, so that the distal tip of the catheter would ordinarily collide with stenosis 24.

In accordance with preferred embodiments of the present invention, however, as shown in FIG. 1B, a sensor 28 at the distal end of catheter 20 senses the presence of an obstruction and/or variations in the velocity of blood flow, as described below. Preferably sensor 28 comprises at least one ultrasound transducer, but it may also comprise a proximity detector, a pressure sensor, a video device, such as a CCD array, other types of optical or infrared detectors, or other detectors useful in sensing obstructions and/or flow velocity, as are known in the art. The sensor preferably detects obstructions and/or flow in a range of 1 to 5 mm ahead of the distal end of the catheter.

Furthermore, in preferred embodiments of the present invention, information received from sensor 28 is also used in determining the direction toward which the distal end of catheter 20 should be deflected, so as to avoid its collision with stenosis 24 and allow it to pass through the clear area of blood vessel 22. Thus, based on the information received from sensor 28, deflection device 30 causes the distal end of catheter 20 to deflect upwards, as shown in FIG. 1B to avoid collision with stenosis 24.

In other preferred embodiments of the present invention, sensor 28 comprises a position sensor, which allows the coordinates of the distal tip of catheter 20 to be determined relative to an external frame of reference. A map or image of the blood vessels through which the catheter is to pass is acquired by angiography, MRI or other methods, known in the art, and is registered with the frame of reference relative to which the coordinates of the tip are to be determined. As the catheter is advanced through vessel 22, its position is tracked, using the position sensor, relative to the map or image, and deflection device 30 deflects the distal tip of catheter 20 so as to steer it along a desired path through the vessel and to avoid collision with stenosis 24.

The position sensor preferably comprises one or more coils, which generate signals in response to an externally-applied magnetic field, as described, for example in U.S. Pat. No. 5,391,199 and PCT patent application number PCT/US95/01103, filed Jan. 24, 1995, which are assigned to the assignee of the present application and whose disclosures are incorporated herein by reference. Other types of position sensors, known in the art, may similarly be used, however.

Alternatively or additionally, the position sensor may be used in a similar manner in conjunction with other previously-acquired and stored data regarding features of the blood vessels through which the catheter is to pass. Such data may include, for example, information regarding the positions of curves, bifurcations and/or obstructions in the blood vessels, measured or otherwise acquired during an earlier catheterization or a surgical procedure.

Furthermore, a plurality of position sensors, or a combination of position sensors and bend sensors, preferably distributed along the length of a distal portion of catheter 20, may be used to determine not only the position of the catheter's distal tip, but also the course of the entire distal portion within the body, preferably as described in the above-mentioned U.S. Provisional Patent Application Ser. No. 60/034,703. Knowing the course of the distal portion of the catheter is useful both in registering the catheter position with a map of a physiological lumen, as described above, and in determining the position of the catheter within a larger physiological cavity, for example, a chamber of the heart.

Figure 2:
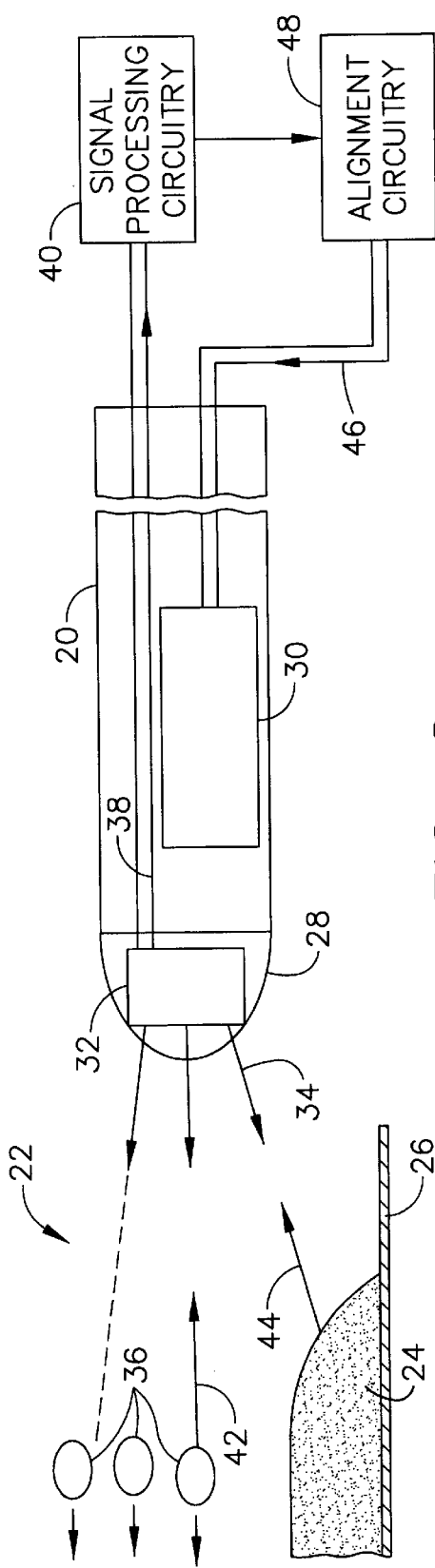
FIG. 2 is a schematic representation of a catheter in accordance with a preferred embodiment of the present invention illustrating its operation.

FIG. 2 shows an expanded view of portions of catheter 20 and blood vessel 22, shown in FIGS. 1A and 1B for a preferred embodiment of the present invention. In the embodiment of FIG. 2, sensor 28 comprises a miniature ultrasound transducer 32, of a type known in the art, which emits an ultrasound beam 34 having a suitable angular extent. Ultrasound waves from transducer 32 strike stenosis 24, as well as blood cells 36, and are reflected back to the transducer. Some of these reflected waves, such as those indicated by arrows 42 and 44, are received by transducer 32, which responds by generating electrical signals, which are conveyed by wires 38 to signal processing circuitry 40.

Because stenoses generally scatter and reflect ultrasound waves much more strongly than does blood, stenosis 24 ahead of catheter 20 causes a reflection of waves 44 back to transducer 32 that is interpreted by signal processing circuitry 40 to indicate the immediate presence of an obstruction (or curve). Upon detection of such an obstruction, the catheter may be steered manually or automatically so as to avoid collision therewith.

In the preferred embodiment of the present invention shown in FIG. 2, signal processing circuitry 40 drives alignment circuitry 48 to transmit steering signals through control channel 46 to deflection device 30, causing it to deflect the distal tip of catheter 20 (as shown in FIG. 1B). Deflection device 30 and control channel 46 may be in accordance with any of the preferred embodiments described below, or they may be of any other suitable types known in the art, for example, mechanical or electronic. Preferably the deflection of the distal tip is varied until a direction of deflection is found that gives a reflection signal that is minimal or below a predetermined threshold. Alternatively, transducer 32 or beam 34 may be scanned laterally so as to find an appropriate deflection direction. The catheter is then moved ahead through the open area of the blood vessel.

Blood cells 36 will typically cause smaller reflections 42, which will be Doppler shifted in frequency relative to the original frequency of beam 34. As is well known in the art, the degree of Doppler shifting is proportional to the speed of motion of cells 36 relative to transducer 32. Signal processing circuitry 40 receives and processes the Doppler-shifted reflected signals, and determines the velocity of blood flow ahead of catheter 20.

Figure 3:
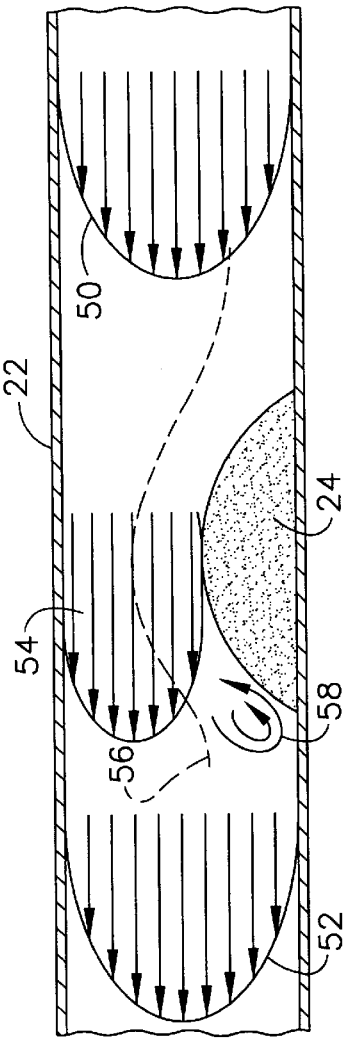
FIG. 3 is a schematic illustration of blood flow velocities in a blood vessel, useful in understanding the operation of preferred embodiments of the present invention.

As shown in FIG. 3, the velocity of blood flow, measured across a cross-section of blood vessel 22, is generally greatest at the center of the area of clear flow, as indicated by the lengths of the arrows in the figure. In unobstructed portions of the blood vessel, as indicated by velocity profiles 50 and 52, an axis of greatest flow 56 is defined by the blood flow and is substantially aligned with the central axis of the blood vessel. Adjacent to stenosis 24, however, axis 56, as defined by velocity profile 54, deviates from the blood vessel's central axis.

When the distal tip of catheter 20 is aligned with axis of greatest flow 56, the Doppler shift of reflection signals received by transducer 32 will be maximized. Therefore, in preferred embodiments of the present invention, signal processing circuitry 40 detects the Doppler-shifted signals received from transducer 32, and drives alignment circuitry 48 to transmit steering signals through channel 46 to deflection device 30, causing it to alien the distal tip of catheter 20 with axis 56. In this way the catheter avoids collision with obstructions such as stenosis 24.

It will be appreciated that maintaining alignment of the distal tip of catheter 20 with axis 56 will also be useful in steering the catheter through curves in blood vessel 22. Sensor 28 and deflection device 30 thus act as a closed-loop servo system, which maintains the distal end of catheter 20 in a desired position, preferably at or adjacent to axis 56.

It will further be appreciated that downstream of obstructions such as stenosis 24, blood flow is typically characterized by turbulence, as indicated by arrows 58 in FIG. 3. This turbulence is detected by signal processing circuitry 40 as a broadening of the Doppler-shifted frequency spectrum. This turbulence is useful as an additional indicator of the presence of an obstruction upstream of the catheter.

Transducer 32 may be driven to emit either a continuous or a pulsed ultrasound beam 34. In preferred embodiments of the present invention using a pulsed beam, signal processing circuitry 40 is time-gated, using methods known in the art, in order to determine the distance from which reflected beams 42 and 44 are reflected back toward the transducer. Time gating thus enables circuitry 40 to determine the distance from catheter 20 to obstruction 24, and to discriminate among cells 36 at various distances ahead of catheter 20 so as to determine blood flow velocity as a function of distance ahead of the catheter.

Figure 4:
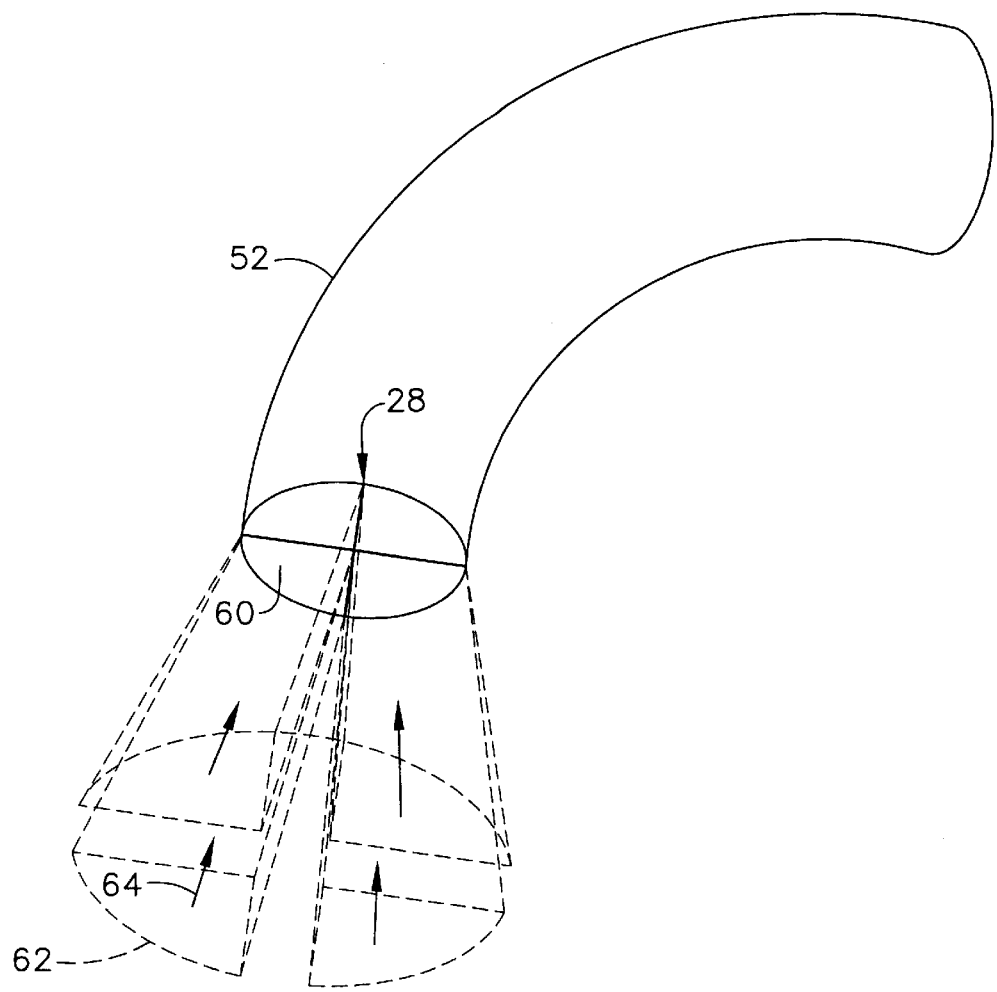
FIG. 4 is a schematic, isometric representation of a catheter having a sensor array at its distal end, in accordance with a preferred embodiment of the present invention.

FIG. 4 shows another preferred embodiment of the present invention, wherein sensor 28 comprises four ultrasound transducers 60, arrayed so as to function as quadrant detectors. Each of the transducers is preferentially responsive to reflected waves from a respective preferred direction 64, so that the signals received therefrom are indicative of objects in a respective quadrant 62 ahead of catheter 20. Signal processing circuitry 40 drives alignment circuitry 48 and deflection device 30 so as to urge the distal end of the catheter away from a quadrant in which a strong reflection signal was received, indicating the presence of an obstruction there, or toward the quadrant in which Doppler signals indicated that blood velocity is greatest.

It will be appreciated that although, for simplicity, the preferred embodiment of sensor 28 shown in FIG. 2 includes a single transducer, while that shown in FIG. 4 includes four transducers, in other preferred embodiments of the present invention (not shown in the figures), sensor 28 may include two, three or more ultrasound transducers. The sensor may further be a mechanically-driven scanning sensor or a phased array scanning sensor.

In one such preferred embodiment of the present invention, sensor 28 comprises a transducer array, which is used to generate an ultrasound image of the blood vessel ahead of catheter 20. This image is analyzed to identify obstructions in the blood vessel and drive alignment circuitry 48 so as to avoid collision with the obstructions.

Figure 5:
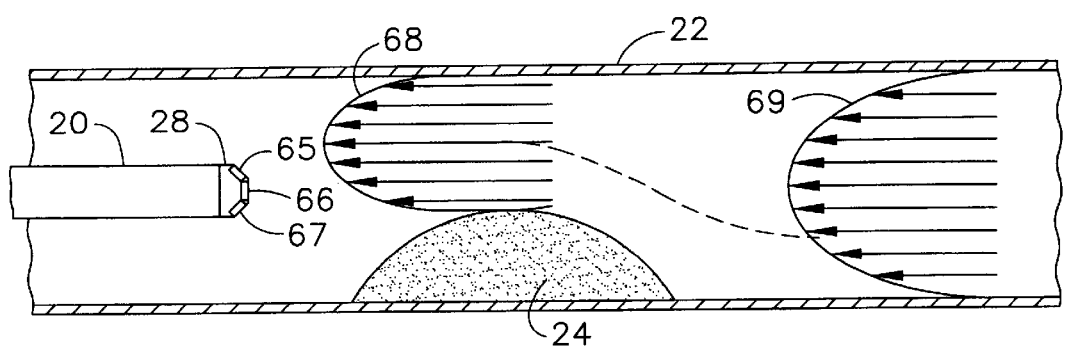
FIG. 5 is a schematic representation of a catheter in an artery, in accordance with a preferred embodiment of the present invention.

As shown in FIG. 5, in another preferred embodiment of the present invention, sensor 28 at the distal end of catheter 20 comprises an array of pressure detectors 65, 66 and 67, oriented at different angles with respect to the long axis of the catheter. Blood vessel 22 in FIG. 5 represents an artery, in which pressure waves 68 and 69 propagate continually downstream as a result of the pulsatile force of the heart beat. The leading edges of these pressure waves will generally pass through a clear portion of vessel 22, away from stenosis 24. Pressure detectors 65, 66 and 67 are used to determine the location of the leading edge of wave 68, so that catheter 20 may be guided toward this location and away from the stenosis. It will be appreciated that in the preferred embodiment shown in FIG. 5, an array of three pressure detectors is shown by way of example only, and other preferred embodiments having fewer or more pressure detectors may similarly be described.

It will be appreciated that the above-described aspects of the present invention will be useful in conjunction with any suitable catheter steering mechanisms known in the art, including both manual and automatic steering mechanisms. The preferred embodiments described below, however, are particularly useful in automatically steering a catheter in conjunction with a sensor at the catheter's distal end, as described above.

Figure 6A:
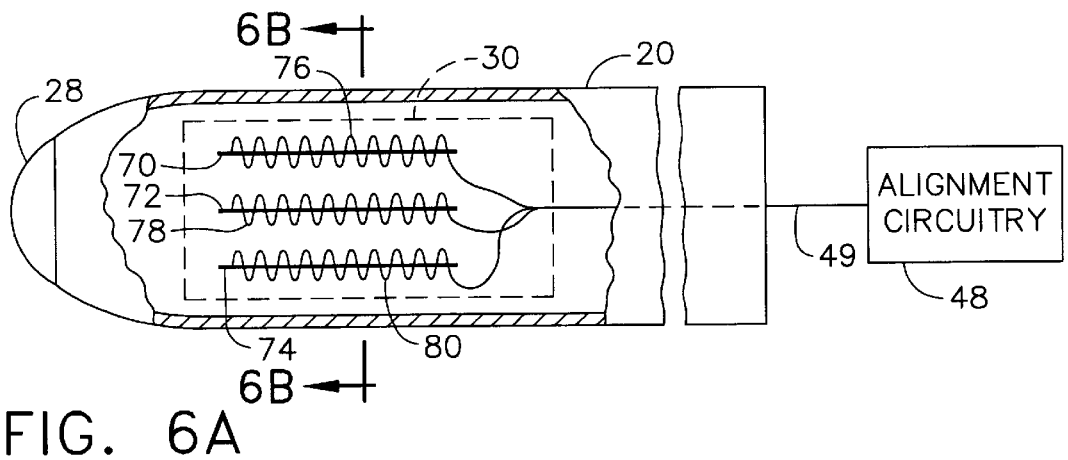
FIG. 6A is a schematic representation of a catheter in accordance with a preferred embodiment of the present invention.
Figure 6B:
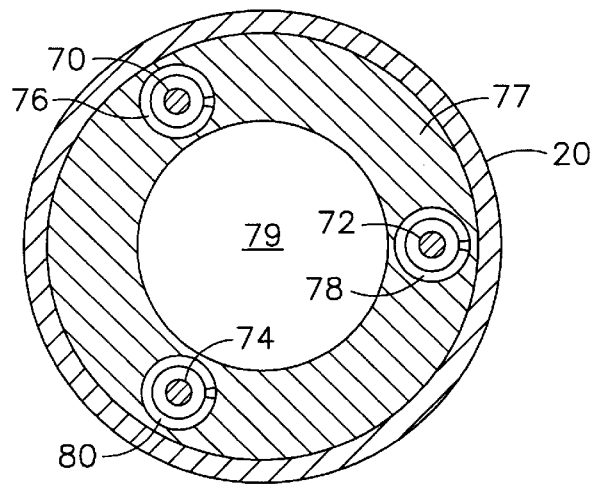
FIG. 6B is a cross-sectional view of the preferred embodiment shown in FIG. 6A.
Figure 6C:
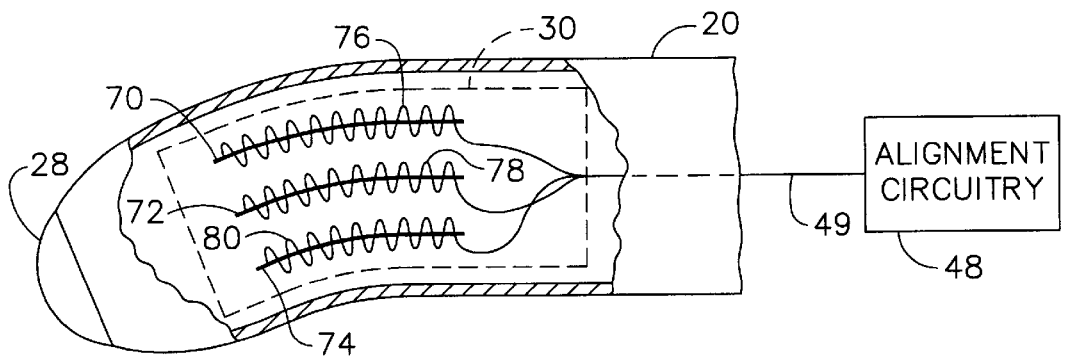
FIG. 6C is a schematic representation of the preferred embodiment shown in FIGS. 6A and 6B, showing deflection of the distal end of the catheter.

Reference is now made to FIGS. 6A–6C, which show details of deflection mechanism 30, in accordance with a preferred embodiment of the present invention. As shown in FIG. 6A, mechanism 30 comprises three bendable elements 70, 72 and 74, preferably made of shape memory material, such as NiTi or other materials known in the art. Elements 70, 72 and 74 are pre-formed so as to remain substantially flexible and straight when their temperatures are below a critical temperature, and to assume a substantially rigid, bent shape when their respective temperatures are above the critical temperature. Heating coils 76, 78 and 80 are wound around elements 70, 72 and 74, respectively, and are connected to alignment circuitry 48 by wires 49. Elements 70, 72 and 74 and their respective heating coils are firmly embedded in catheter 20, for example by molding or gluing them in place, so that any bending of the elements will cause the catheter to bend accordingly. As long as alignment circuitry 48 does not generate electrical currents through wires 49, however, the heating coils remain at ambient temperature, and shape memory elements 70, 72 and 74 remain substantially flexible, so that catheter 20 is maintained in a substantially straight orientation.

FIG. 6B shows a cross-sectional view of the catheter shown in FIG. 6A. As shown in FIG. 6B, elements 70, 72 and 74 are mutually spaced about the long, central axis of catheter 20, so that each of the elements may conveniently control the deflection of the tip of the catheter, as will be explained below. The elements are embedded in a solid, flexible, annular portion 77 of catheter 20, which surrounds a central lumen 79.

As shown in FIG. 6C, when it is desired to deflect the distal end of catheter 20, for example to avoid collision with stenosis 24, as shown in FIG. 1B, an electrical current is supplied by alignment circuitry 48 to at least one of the heating coils, for example coil 76. Shape memory element 70 is heated and assumes its substantially rigid, bent shape, thereby causing catheter 20 to deflect. Elements 72 and 74 remain substantially flexible, and so bend along with element 70.

FIGS. 7A and 7B show another preferred embodiment of the present invention, wherein tip deflection mechanism 30 comprises two bendable bimetal elements 82 and 84, of types known in the art, which bend or straighten in response to changes in temperature. As described in regard to the preferred embodiment of FIGS. 6A–6C, elements 82 and 84 are firmly embedded in annular portion 77 of catheter 20, so that when the elements bend, they cause the catheter to bend accordingly. As shown most clearly in FIG. 7B, elements 82 and 84 are preferably arranged in catheter 20 at right angles, so as to control the catheter's bending about respective axes that are mutually substantially orthogonal. As shown in FIG. 7A, elements 82 and 84 are preferably mutually offset, so as to allow both elements to bend freely as required. Such mutual offset is required in the embodiment of FIGS. 7A–7B, because the relatively large widths of elements 82 and 84 prevent their bending freely in any directions other than about their respective bending axes (unlike elements 70, 72 and 74 in FIGS. 6A–6C, which may bend relatively freely in any desired direction so long as they are below their critical temperature).

The tip deflection mechanism further includes heating and/or cooling elements 86, coupled to alignment circuitry 48 by wires 46, as described above. Elements 86 may include any suitable heating devices, such as heating coils, and/or any suitable cooling devices, such as miniature Peltier coolers, as are known in the art. Heating and/or cooling elements 86 control the respective bend angles of the bimetal elements, so as to straighten or deflect the distal end of the catheter.

Figure 8:
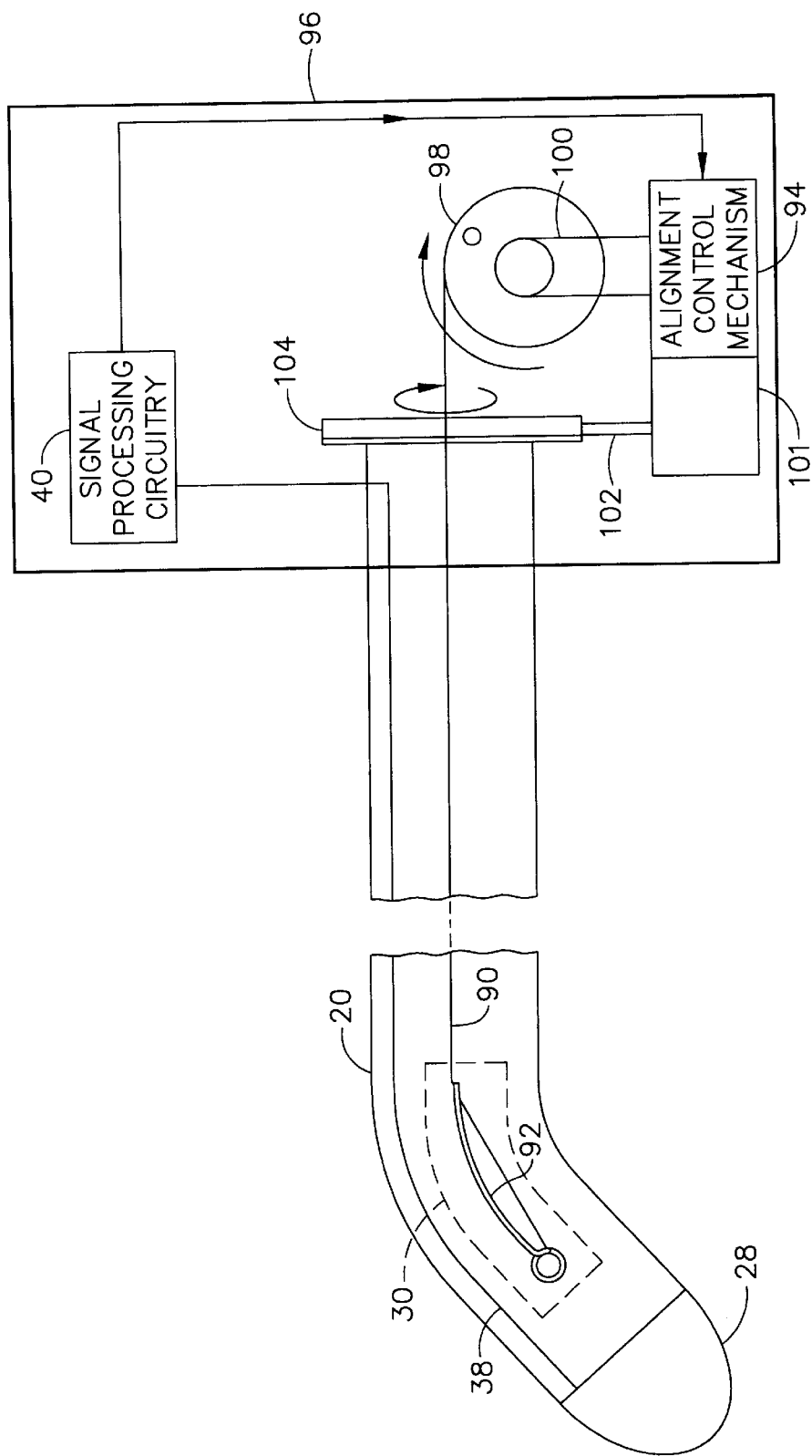
FIG. 8 is a schematic representation of a catheter and a catheter control unit, in accordance with a preferred embodiment of the present invention.

FIG. 8 shows still another preferred embodiment of the present invention, in which tip deflection mechanism 30 comprises a mechanical pull-wire 90 and a bendable element 92. Pull-wire 90 is coupled distally to bendable element 92 and proximally to alignment control mechanism 94, which is preferably contained in control unit 96. Mechanism 94 applies a variable tension to the pull-wire by means of pulley 98 and linkage 100, thereby causing bendable element 92 to bend. Bendable element 92 is made of a resilient material, for example spring steel or other materials known in the art, and is formed so as to maintain catheter 20 in a substantially straight alignment when the tension in pull-wire 90 is released.

Since mechanism 30 shown in FIG. 8 can cause catheter 20 to deflect in only a single direction, for example up and down, as illustrated in FIG. 8, alignment mechanism includes rotation control mechanism 101, which is coupled via linkage 102 to wheel 104, which controls the rotation of catheter 20 about its long axis. Thus, when signal processing circuitry 40 receives signals from sensor 23 that are indicative of a need to deflect catheter 20 in a given direction, circuitry 40 drives alignment mechanism 94 to rotate the catheter as necessary, via linkage 102 and wheel 104, so that when tension is applied to pull-wire 90 via pulley 98 and linkage 100, the distal end of the catheter will bend in a desired direction.

Although the preferred embodiment of the present invention shown in FIG. 8 includes only a single pull-wire 90, so that mechanism 30 can bend in only a single direction, it will be appreciated that in other preferred embodiments of the present invention, based on similar mechanical principles, two or more pull-wires could be used, so that mechanism 30 will have a greater range of bending angles and directions.

FIGS. 9A–9C show still another preferred embodiment of the present invention, wherein distal tip deflection mechanism 30 comprises piezoelectric stacks 106, 108, 110 and 112. Each of stacks 106, 108, 110 and 112 comprises a plurality of piezoelectric crystals 114, as are known in the art, alternating with and coupled by bendable joints 116. The bendable joints are preferably made of a resilient material, for example spring steel, which bends, but does not substantially compress, when a force is applied thereto.

As illustrated by FIG. 9A, piezoelectric stacks 106, 108, 110 and 112 (of which only stacks 106 and 110 are shown in this cross-sectional view) are formed so as to maintain the distal end of the catheter in a substantially straight orientation, so long as no obstruction is detected immediately ahead of the catheter. When an obstruction is detected, however, alignment circuitry 48 applies a voltage via wires 46 to piezoelectric crystals 114 in at least one of the piezoelectric stacks, so as to alter the overall length of the stack and thereby deflect the distal end of the catheter. Thus, as shown in FIG. 9B, a voltage is applied to crystals 114 in stack 106, causing these crystals to lengthen relative to counterpart crystals 114 in stack 110, thereby deflecting the distal tip of catheter 20 downwards.

As shown in FIG. 9C, one pair of piezoelectric stacks 106 and 110 are counterposed to control up-and-down motion of the distal end of catheter 20, and the other pair 108 and 112 are counterposed to control left-right motion.

The principles of the present invention may similarly be applied to catheters using other types of steering mechanisms, for example a balloon-based bending mechanism, as described in U.S. Pat. No. 4,983,165, and incorporated herein by reference.

Figure 10:
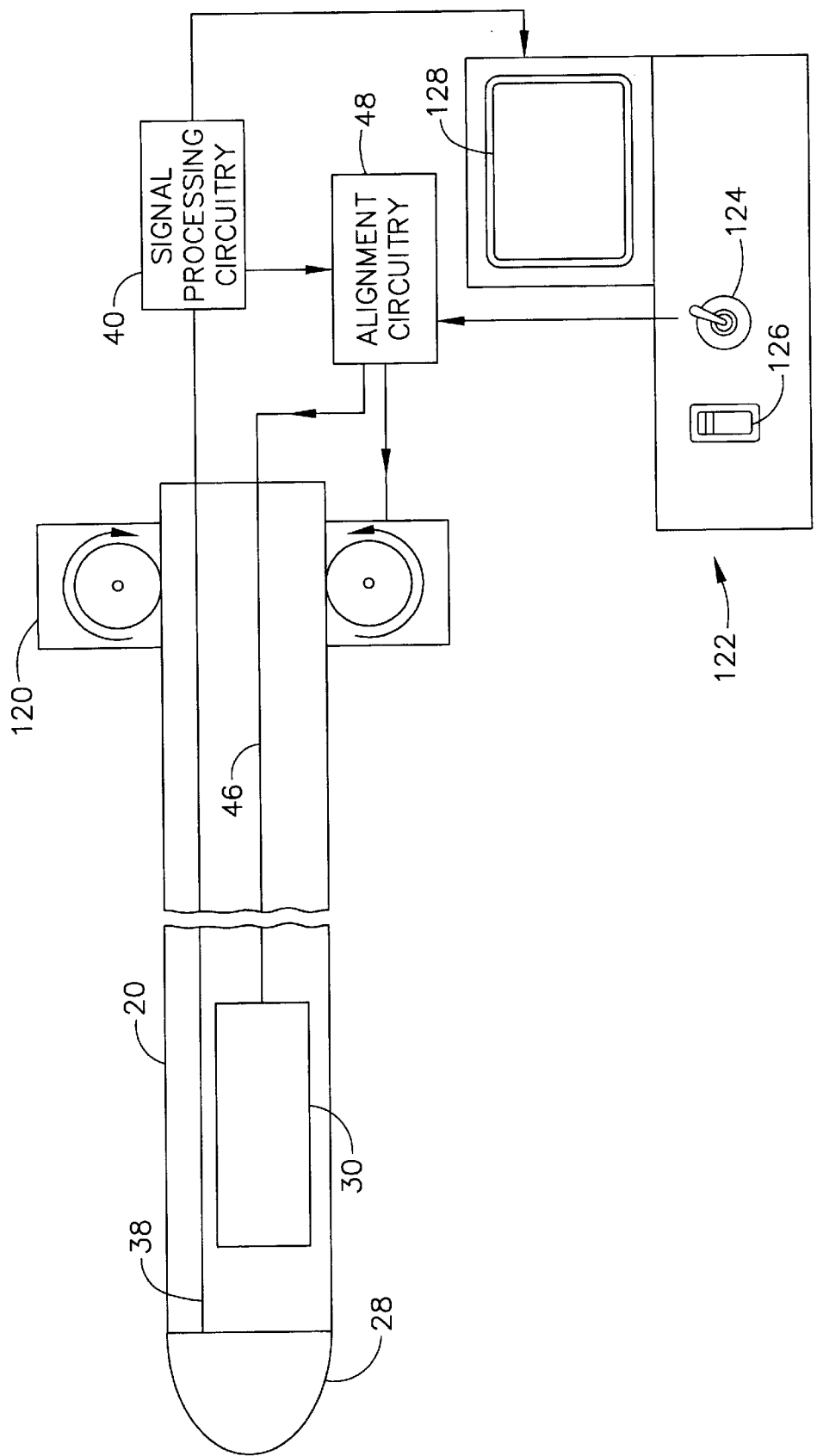
FIG. 10 is a schematic representation of a catheter and catheter controls in accordance with a preferred embodiment of the present invention.

In other preferred embodiments of the present invention, shown for example in FIG. 10, catheter 20 is further coupled to a catheter advance mechanism 120, which is controlled by alignment circuitry 48 so as to advance the catheter gradually through the blood vessel while avoiding collision with obstructions, as described above. When signal processing circuitry 40 receives signals from sensor 28 that are indicative of an obstruction ahead of catheter 20, it preferably drives alignment circuitry 48 to slow or stop the advance of the catheter until it has been suitably aligned in a clear channel bypassing the obstruction, after which forward motion of the catheter is resumed.

Furthermore, as further illustrated in FIG. 10, in some preferred embodiments of the present invention, alignment circuitry 48 (or control unit 96, as shown in FIG. 8) includes an operator interface unit 122. Preferably unit 122 includes a steering control 124, such as a joystick, which enables the operator to steer catheter by controlling distal tip deflection mechanism 30, and a catheter advance control 126, such as a toggle switch, which enables the operator to control catheter advance mechanism 120. Unit 122 also preferably includes a display 128, which presents information received from signal processing circuitry 40 regarding the channel ahead of catheter 20. An operator may use interface unit 122 in addition to or instead of automatic steering of the catheter by alignment circuitry 48. The interface unit is particularly useful in allowing the operator to override the automatic tip deflection and catheter advance mechanisms described above, so as to guide the catheter in a desired direction when the catheter approaches a bifurcation of the blood vessel, for example. Operator control of distal tip deflection mechanism 30 in accordance with preferred embodiments of the present invention may be instead of or in addition to the use of conventional catheter steering systems, as are known in the art.

Although the above preferred embodiments have been described with reference to intravascular catheters, it will be appreciated that the inventive principles of the present invention may similarly be applied to catheters, endoscopes and other devices that are inserted into other physiological orifices and lumens, including but not limited to the digestive tract, the urinary tract, the reproductive system, and nasal and sinus passages.

Moreover, the principles of the present invention may also be applied to produce self-aligning probes for insertion through physiological tissues and cavities of other types. Such probes may comprise sensors which detect characteristics of fluid flow and/or pressure and/or solid obstructions in the path of the probe, as described above. Alternatively or additionally, the probes may include sensors of other types, for example, chemical sensors or electrical sensors, as are known in the art. Thus, in one exemplary embodiment of the present invention, a probe for insertion into the liver of a subject comprises a chemical sensor adjacent its distal end, which may be used for detecting elevated hormonal activity, for example, and a self-alignment mechanism, as described above, for guiding the probe toward a source of the hormonal activity.

It will moreover be appreciated that the elements of the preferred embodiments described above, and in particular, the various types of sensors and alignment mechanisms, as well as other sensors and mechanisms known in the art, may be used together in other combinations and configurations. For example, multiple sensors of different types may be combined in a single self-aligning catheter. The preferred embodiments described above are cited herein by way of example, and the full scope of the invention is limited only by the claims.

What is claimed is:

1. A flexible, elongate probe having a distal end for insertion through physiological tissue, comprising:

a sensor, which generates sensor signals indicative of a characteristic of the tissue in a vicinity of the probe;

signal processing circuitry for receiving the sensor signals;

alignment circuitry operatively connected to the signal processing circuitry for transmitting a steering signal in response to the signal processing circuitry; and an alignment mechanism, which deflects the distal end of the probe in response to the steering signal from the alignment circuitry.

2. A probe according to claim 1, wherein the probe comprises a catheter for insertion through a physiological lumen, and wherein the sensor generates the signals responsive to a characteristic of the lumen ahead of the catheter.

3. A probe according to claim 2, wherein the signals are indicative of of a pressure in the tissue.

4. A probe according to claim 3, wherein the signals are indicative of a gradient of the pressure.

5. A probe according to claim 4, wherein the alignment mechanism drives the probe toward the leading edge of a pressure wave in the tissue.

6. A probe according to claim 5, wherein the signals are indicative of a gradient of the flow.

7. A probe according to claim 6, wherein the signals are indicative of turbulence of the flow.

8. A probe according to claim 7, wherein the alignment mechanism drives the probe toward an area of high flow velocity.

9. A probe in accordance with claim 2, wherein the sensor comprises at least one ultrasound transducer.

10. A probe according to claim 9, wherein the signals are indicative of a gradient of the pressure.

11. A probe in accordance with claim 10, wherein the signal processing circuitry detects a Doppler shift in the ultrasound waves received by the sensor.

12. A probe in accordance with claim 2, wherein the alignment mechanism comprises a plurality of deflection elements, each of which deflects the prove in one of a plurality of respective directions.

13. A probe in accordance with claim 12, wherein the alignment mechanism comprises one or more deflection elementss that deflects the distal end of the probe and a rotation element that rotates the probe about its long axis.

14. A probe in accordance with claim 13, wherein at least one of the deflection elements comprises a bendable element.

15. A probe in accordance with claim 14, wherein the bendable element comprises superlastic material.

16. A probe in accordance with claim 14, wherein the bendable element comprises a bimetal element.

17. A probe in accordance with claim 14, wherein the bendable element bends or straightens in response to an electrical drive signal.

18. A probe in accordance with claim 17, wherein the electrical drive signal causes a change in the temperature of the bendable element 19. A probe in accordance with claim 18, and comprising a heating element, associated with the bendable element, which receives the electrical drive signal.

20. A probe in accordance with claim 19, and comprising a cooler, associated with the bendable element, which receives the electrical drive signal.

21. A probe in accordance with claim 14, and comprising at least one mechanical pull-wire coupled to the bendable element.

22. A probe in accordance with claim 21, wherein the bendable element bends in response to tension in the pull-wire.

23. A probe in accordance with claim 13, wherein at least one of the deflection elements comprises at least one piezoelectric stack.

24. A probe in accordance with claim 23, wherein the stack comprises a plurality of piezoelectric crystals, coupled by a plurality of bendable joints.

25. A probe in accordance with claim 24, wherein the stack bends in response to an electrical signal applied thereto.

26. A probe in accordance with claim 2, wherein the signals are indicative of obstructions in the lumen.

27. A probe in accordance with claim 26, wherein te signals are indicative of the direction of a clear channel in the lumen.

28. A probe according to claim 26, wherein the signals are indicative of a fluid flow in the tissue.

29. A probe according to claim 28, wherein the signals are indicative of a gradient of the flow.

30. A probe according to claim 29, wherein the signals are indicative turbulence of the flow.

31. A probe according to claim 30, wherein the alignment mechanism drives the probe toward an area of high flow velocity.

* * * * *